United States Patent
Trenholm

(10) Patent No.: US 7,100,423 B2
(45) Date of Patent: Sep. 5, 2006

(54) METHOD AND APPARATUS FOR MONITORING PARTICLES IN A FLOWING GAS

(75) Inventor: Andrew R. Trenholm, Raleigh, NC (US)

(73) Assignee: Midwest Research Institute, Kansas City, MO (US)

( * ) Notice: Subject to any disclaimer, the term of this patent is extended or adjusted under 35 U.S.C. 154(b) by 191 days.

(21) Appl. No.: 10/655,420

(22) Filed: Sep. 4, 2003

(65) Prior Publication Data

US 2005/0050968 A1    Mar. 10, 2005

(51) Int. Cl.
G01N 15/02 (2006.01)
(52) U.S. Cl. ..................................... 73/28.02
(58) Field of Classification Search ............... 73/865.5, 73/28.02; 324/455, 464, 71.4, 453
See application file for complete search history.

(56) References Cited

U.S. PATENT DOCUMENTS

| | | | |
|---|---|---|---|
| 4,531,402 A * | 7/1985 | Reif et al. ................. | 73/28.02 |
| 4,873,970 A | 10/1989 | Freidank et al. | |
| 5,287,061 A * | 2/1994 | Dechene et al. ............ | 324/454 |
| 5,552,324 A | 9/1996 | Liu | |
| 5,571,945 A | 11/1996 | Koutrakis et al. | |
| 5,932,795 A | 8/1999 | Koutrakis et al. | |
| 5,983,732 A | 11/1999 | Hering et al. | |
| 6,011,479 A | 1/2000 | Morgan et al. | |
| 6,016,688 A * | 1/2000 | Hiss et al. ................. | 73/28.01 |
| 6,187,596 B1 | 2/2001 | Dallas et al. | |
| 6,248,153 B1 | 6/2001 | Braun et al. | |
| RE37,353 E | 9/2001 | Kreikebaum et al. | |
| 6,405,135 B1 | 6/2002 | Adriany et al. | |
| 6,425,297 B1 | 7/2002 | Sharp | |
| 6,489,775 B1 * | 12/2002 | Rigby et al. ................. | 324/454 |
| 2001/0015408 A1 | 8/2001 | Stock | |
| 2002/0074279 A1 | 6/2002 | Van Pelt et al. | |
| 2002/0092525 A1 | 7/2002 | Rump et al. | |

OTHER PUBLICATIONS

Midwest Research Institute, "Fabric Filter Bag Leak Detection Guidance," pp. 1-20, Sep. 1997.
Anderson, J.W., "Revising The Air Quality Standards" Resources For The Future Library issue Brief, pp. 2-16, [retrieved from Internet on Oct. 15, 2002] Retrieved from the Internet http://222.trr.org/issue_briefs/pdf_files/NAAQS_primer.htm.
U.S. Environmental Protection Agency, Technology Transfer Network OAR Policy And Guidance, "Fact Sheet—EPA's Recommended Final Ozone And Particulate Matter Standards" pp. 1-3, [retrieved from Internet on Oct. 15, 2002], Retrieved from the Internet: http://www.epa.gov/ttn/oarpg/naaqsfin/o3pm.html.
U.S. Environmental Protection Agency, Technology Transfer Network OAR Policy And Guidance, "EPA's Decision On New Air Quality Standards" pp. 1-3, [retrieved from Internet on Oct. 15, 2002, clean copy on Jul. 26, 2005], Retrieved from the Internet: http://www.epa.gov/ttn/oarpg/naaqsfin/.
U.S. Environmental Protection Agency, Air & Radiation, "National Ambient Air Quality Standards" [retrieved from Internet on Oct. 15, 2002, clean copy on Jul. 26, 2005], Retrieved from the Internet: http://www.epa.gov/airs/criteria.html.

(Continued)

Primary Examiner—Robert Raevis
(74) Attorney, Agent, or Firm—Lathrop & Gage, LC

(57) ABSTRACT

A method and apparatus for monitoring particulate matter in a gas sample and the air quality associated therewith is provided.

23 Claims, 3 Drawing Sheets

OTHER PUBLICATIONS

NYS Department of Environmental Conservation, "PM 2.5 Monitoring" pp. 1-2, [retrieved from Internet on Oct. 15, 2002], Retrieved from the Internet: http://www.dec.state.ny.us/website/dar/baqs/pm25mon.html.

NYS Department of Environmental Conservation, "New York State Ambient Air Monitoring System" pp. 1-4, [retrieved from the Internet on Oct. 15, 2002] Retrieved from the Internet: http://www.dec.state.ny.us/website/dar/bts/airmon/parametertextpage1.htm.

Ramsey, Kay, "The Emergence of Triboelectric Technology", Pollution Engineering, pp. 1-5, Sep. 1998.

Cheng, L. and Soo, S.L., "Charging Of Dust Particles by Impact" Journal of Applied Physics, vol. 41, No. 3, pp. 585-591, Feb. 1970.

John, Walter, PhD., "Contact Electrification Applied to Particulate Matter-Monitoring" Fine Particles, pp. 650-667, 1976.

United States Enviromental Agency, Office of Air Quality Planning And Standards, "Current Knowledge of Particulate Matter (PM) Continous Emission Monitoring" EPA-454/R-00-039, pp. 1-A2, Sep. 8, 2000.

Grindell, D.H., "Atmospheric Pollution By Solid Particles, Measuring Significant Particle Surface Area by Charge Transfer" Engineering, pp. 350-351, Mar. 13, 1959.

* cited by examiner

METHOD AND APPARATUS FOR MONITORING PARTICLES IN A FLOWING GAS

FIELD OF THE INVENTION

This invention relates generally to a method and apparatus for monitoring airborne particles in a flowing gas.

BACKGROUND

Particulate matter (particulates) is the generic name used to describe small particles of solid or semi-solid materials, liquid droplets, aerosols and combinations thereof that are present in the ambient air. Total suspended particulates (TSP) refer to those airborne particulates that are less than 100 microns in diameter, which is the approximate thickness of a typical human hair. Particulates less than 10 microns in diameter are designated as $PM_{10}$. Particulates originate from many sources, including combustion; poor industrial dust containment of such materials as coal dust, fly ash, and carbon black; automotive exhaust, especially diesel; and windblown or fugitive dust from roadways, fields, construction sites, and soil erosion. Photochemical reactions of certain gaseous pollutants in the presence of ultraviolet light also produce airborne particulates in the form of aerosols. These aerosols tend to be less than one micron in diameter. This is smaller in size than either fugitive dust or particulates from industrial sources, which tend to be greater than one micron in diameter.

Particle size distributions can affect visibility, as well as human respiratory functions. Those particles with diameters in the size range of 0.1 to 1.0 microns are the most efficient at scattering visible light which is, generally, light having a wavelength from about 0.4 to 0.7 microns. This scattering is a primary contributor to reduced visibility. When these particles combine with water vapor at high humidity they may, for example, create haze and smog. Larger particles, in the range of 0.5 to 5.0 microns, can be inhaled but are normally deposited in the bronchi before reaching the alveoli or air sacks of the lungs. With the exception of fibrous materials such as asbestos, particles smaller than 0.5 microns, are generally understood to be capable of reaching the avioli.

In addition to reducing visibility and causing respiratory problems, cancer, and heart attacks, airborne particulates can cause corrosion of metals and electrical equipment, as well as soiling of textiles and building materials.

Epidemiological studies in the U.S. and abroad have shown associations between mortality and morbidity and human exposure to ambient particulate matter (Schartz and Dockery, Am. Rev. Resp. Dis. 145:600, 1992; Pope et al., Am. Rev. Resp. Dis. 144:668, 1992). To date, there is limited knowledge about the physical or chemical property of particulate matter that is responsible for these health effects. In addition, there is an increasing interest in developing accurate measurements for particulate matter.

In order to determine air quality, the air may be monitored. Monitoring may be effected in a variety of ways. Typically, samples of air are collected at specific locations for a given period of time, followed by the analysis of the samples using any number of known analytical techniques.

The United States Environmental Protection Agency (EPA) recognizes a need to develop techniques for the continuous measurement of inhalable particulate matter, such as PM10 and PM2.5, which are particulate matter of less than 10 microns and 2.5 microns in diameter, respectively. The majority of the current particulate mass measurement methods use a size selective inlet to remove particles above a certain size, usually 10 microns in diameter (PM10). Most of the available data on PM10 and PM2.5, have been obtained using gravimetric methods. The collected particles are weighed using microbalances under constant specified temperature and relative humidity conditions. However, gravimetric methods are not sensitive enough to measure samples collected in short periods needed to provide a continuous measurement.

The Tapered Element Oscillating Microbalance (TEOM) is a recently developed method that originally appeared to be very promising, as reported in Patashnick and Rupprecht, Continuous PM-10 Measurements Using the Tapered Element Oscillating Microbalance, J. Air Waste Manage. Assoc. 41:1079, (1991). According to this method, the air sample is heated up to 50° C. to remove moisture, and particles are subsequently collected on a TEFLON® filter that oscillates at the top of a metal rod. The amplitude of the oscillation decreases as the mass of the particles collected on the filter increases. Although this method is highly sensitive, measurements are subject to a number of interferences. Significant losses occur for semivolatile organic and inorganic compounds that in some areas can represent relatively large fraction of the total particulate matter. This problem is more pronounced for PM2.5, which includes unstable compounds such as ammonium nitrate and carbonaceous aerosols. For areas such as California and large urban environments, this method may significantly underestimate particle mass concentrations. Also, as the composition of the air sample changes, the partitioning of air pollutants between the gas and particle phase changes. Therefore, absorption and/or desorption processes can take place on the filter, depending upon whether the air sample becomes more or less polluted. Due to the sensitivity of the method, these phenomena can cause either negative or positive artifacts. The gains and losses of mass on the filter are a serious problem, not just of the TEOM, but of any method that collects particles on a filter over a prolonged period of time, for example, over a period of days. Finally, this method presents oscillations or noise in its response. The noise cancels out if a large number of measurements are added to determine a multi-hour concentration estimate; however, over shorter time intervals the measurement errors due to this oscillation can exceed 20–30%.

Short-term measurement of particle size distributions is at least as important as short-term measurement of total particle mass concentrations. In fact, particle size distribution is frequently the most important measurement parameter, since the majority of the physical processes governing the behavior of particles depend on particle size. Particle sizes vary with particle sources, formation mechanisms, and chemical composition. The airborne lifetime of particles is affected by particle sizes. Moreover, the uptake, retention and clearance of particles by the human respiratory system is a function of particle size. Thus, obtaining short-term measurements of particle size distribution, particularly those with diameters smaller than 2.5 microns, could substantially improve exposure assessment and, thus, environmental or regulatory decision-making.

To date, there is no adequate monitoring technique that determines the size distribution of particles based on mass on a continuous basis. Quartz crystal piezobalances are commonly used to determine particulate mass indirectly through particle impaction on an oscillating quartz surface, as reported in Lundgren, D. A., In Fine Particles, edited by B. Y. H. Liu, Academic Press Inc., New, York, (1976); and Chuan, R. L., In Fine Particles, edited by B. Y. H. Liu, Academic Press Inc., New, York, (1976). In these devices, a quartz disk oscillates in an electric circuit at a highly stable resonant frequency which is inversely proportional to the particulate mass impacting and adhering onto the quartz disk.

The piezobalances suffer from the various potential shortcomings. First, the relationship between frequency and mass becomes non-linear for high particulate loadings. Second, since the quartz disk collects particles by impaction, the instrument response depends upon the sharpness of collection efficiency, for example, as affected by the extent of particle bounce and internal particle losses. Finally, carbonaceous aerosol particles, which are composed of long stable chains of very small primary particles, cannot be determined with piezobalances. These chain aggregates contact the sensor at 2 to 3 points, but most of the particulate mass is suspended above the sensor surface where it cannot be measured, for example, as reported by Lundgren, D. A. and Daley, P. S., Am. Ind. Hyg. Assoc. J., 581–588, 1977.

Other direct-reading methods to determine particle concentration and size distribution include optical and electrical counters. Most of the optical systems count light pulses scattered from particles that flow through an intensely illuminated zone. One limitation is the dependence of the instrument's response on the particle refractive index. Measurement error is introduced where particles vary in composition and refractive index. In addition, the art confronts instrument sensitivity problems requiring complex solutions when ambient air contains particles that are larger and smaller than about 0.2 to 0.3 microns, for example, as reported in U.S. Pat. No. 5,835,211 issued to Wells et al.

Another type of particle counter is the aerodynamic particle sizer (APS), for example, Model 3310 sold by TSI Inc. of St. Paul, Minn., which is described by Wilson, J. C. and Liu, B. Y. H., J. Aersol. Sci. 11:139–150 (1980); and Baron, P., Aerosol Sci. and Technol. 5:56–67, (1985). The APS sizes and counts particles by measuring their time-of-flight in an accelerating flow field. Particle measurement is based on particulate inertia, hence the system determines the aerodynamic particle diameter. The main shortcoming of the APS is that it cannot determine size for particles smaller than about 0.7 microns More generally, electrical counters have been used to determine particle sizes by charging the sampled aerosols and measuring the ability of particles to traverse an electrical field. The most widely used instrument of this type is the Differential Mobility Analyzer (DMA) (Model 3932, TSI Inc., St. Paul, Minn.). This technology is limited to measuring aerosols in the size range 0.01–0.5 microns. Using the DMA in conjunction with an optical counter or the APS would make it possible to determine a broad size range of atmospheric particles. Nevertheless, there are still three other shortcomings. First, both optical and electrical counters determine the number size distribution of particles which they subsequently convert to volume distribution. Since the density of particles varies significantly (in the range of +/−30% of the mean value), and since mass concentration is directly proportional to the density, large uncertainties can result from using these methods to determine particle mass concentrations as a function of size. Second, these techniques require conversion of the size distribution, by number, to a corresponding volume size distribution. The size distribution, by number, of particles is dominated by ultrafine particles (i.e., smaller than 0.1 microns). The coarser the particles, the smaller the concentration becomes. However, when converting a number to volume distribution, a 1.0 micron particle weighs as much as $10^3$ of 0.1 micron particles and $10^6$ of 0.01 micron particles. Counting errors are substantial for large particles, due to their relatively low number concentrations combined with electronic noise in the instrumentation. There are significant uncertainties in volume and, consequently, mass as a function of particle size. Finally, these instruments are very expensive, costing for example up to $100,000 for the combined optical/electrical counter. There are also relatively high maintenance costs, so these devices are generally unsuited for large-scale field studies.

A continuous ambient mass monitor (CAMM) apparatus has been developed at the Harvard School of Public Health, as reported in an Abstract of presentation at conference entitled Measurement of Toxic and Related Air Pollutants, Research Triangle Park, N.C., Cosponsored by the U.S. Environmental Protection Agency and the Air and Waste Management Association, May 7–10, (1995). This apparatus provides for the real time measurement of particulate matter in a gas, and is based on monitoring a pressure drop across a porous membrane filter over a period of time. However, this method is limited to the measurement of the mass of ambient fine particles, generally, less than about 2.5 microns in diameter.

Other particle counters are known, but generally fail to overcome the aforementioned problems of high cost, accuracy and sensitivity. U.S. Pat. No. 5,932,795, issued Aug. 3, 1999, provides a method and apparatus for the continuous monitoring of ambient particle mass in a gas sample using a series of particulate matter collectors where the particle size is from 2.5 to 10 microns. U.S. Pat. No. 5,571,945, issued Nov. 5, 1996, provides a method and apparatus for measuring particulate matter in a gas which employs pressure sensors. U.S. Pat. No. 6,011,479, issued Jan. 4, 2000, provides a personal continuous air monitor capable of sensing radiation. This air monitor employs a filter or detector head with a radiation detector and a series of signal processing units. U.S. Pat. No. 6,187,596, issued Feb. 13, 2001, provides a visual airborne contaminant indicator employing a colored pH indicator, which may be used with an adsorptive filter. U.S. Pat. No. 6,248,153, issued Jun. 19, 2001, provides a diffusional gas transfer system for removing airborne particles.

U.S. Pat. No. 6,431,014 shows a particle measurement device characterized as a cascade impactor. Cascade impactors are generally used for the classification of aerosols according to size and for possible subsequent chemical analysis. Air is drawn through a series of orifices of decreasing size. Air low is usually normal to collecting surfaces on which aerosols are collected by inertial impaction. The particles are separated stepwise by their momentum differences into a number of size ranges, and may be collected simultaneously. One commercially available in-stack cascade impactor is the Graseby Anderson Mark III™ made by Clean Air Analytical Service of Palatine, Ill.

Continuous monitoring of PM concentrations in smoke stacks started during the 1960s in Germany. During the 1970s, studies unsuccessfully attempted to correlate PM concentrations to opacity monitor readings in the United States. More recent studies have evaluated several types of continuous PM monitors including optical, beta gauge, and triboelectric devices. These devices have, with varying degrees of success, continuously monitored total particulate, but have not been used to measure specific size fractions.

It would be a significant contribution to the art to provide an improved, versatile method and apparatus for monitoring the mass of particulate matter in a gas.

SUMMARY

A monitoring system overcomes the problems outlined above and advances the art by providing method and apparatus for monitoring specified size fractions of particulate matter in a gas, for example the mass of particles smaller than 2.5 microns. The monitoring system is relatively inexpensive to build and maintain, has a simple design with no moving parts, and can provide measurements in ducts or stacks with flowing gas.

In one aspect, a signal may be correlated to the total mass or mass flow rate of particles in a gas stream that are below a specific particle size delimiter. Another signal may vary with the total surface area of the particles.

The monitoring system may combine the two signals. For a given mass, surface area increases as the particle size decreases. Thus, combining these signals to provide a ratio of surface area to mass flow provides a signal that increases as particle size decreases. Such a signal, when calibrated, provides a measure of mass less than 2.5 microns or another specified size.

Addition of a blower allows the instrument to be used in low flow situations including ambient air. The signal related to particle mass may be provided by a triboelectric probe. As particles in a gas stream collide with or pass close to the triboelectric probe, a charge transfer generates a detectable current. The current is generally proportional to the particulate mass flow, though it can be affected by a number of factors such as particle composition, velocity, particle size, particle charge, and particle shape. For a given emission source in most environments of use, only two of these factors have a significant effect on the signal to mass relationship. They are: (1) velocity, and (2) particle charge. While triboelectric probes may be used to measure particle content in liquid-saturated gas streams, appreciable error may arise where liquid droplets are present or condensation may occur.

The signal related to particle surface area may be generated in several ways, for example, in laser-based measurement of Mie scattering. A simpler approach is to charge the particles in a high voltage field, such as a corona field, followed by impingement upon a second triboelectric probe. The particles discharge when they contact the probe, and produce a current in the probe proportional to the charge. The charge resides on the surface of the particles and, thus, is proportional to the surface area.

Accordingly, one embodiment of the monitoring system confines a portion of the gas stream in a tube that contains, in series, a first triboelectric probe, a high voltage field, and a second triboelectric probe. If the incoming gas flow stream is substantially homogeneous, it may be divided into a plurality of segments, such that the measurements need not be made in series.

Charge transfer from particles to a probe has been studied as a means to monitor particle mass or size for the last 40 years. "Electrostatic Samplers" have been employed where particles are charged in a high-voltage field and the particles are then deposited on a collecting electrode. Triboelectric monitors have also been used in particulate emission rate monitors.

One type of charge transfer based on the triboelectric principle occurs when two solids come into contact. Particles contacting a sensor placed in a gas stream will generate a current in the sensor that is generally proportional to the particle mass. Several factors such as particle composition, size, shape, and particle charge can effect the generated signal. For a given source, the effects should be small except where there are large changes in velocity or electric field strengths. In addition to the charge generated by particles contacting the sensor, a current is also introduced in the sensor as particles pass near the probe. This type of charge transfer is generally referred to as electrostatic induction.

An additional discussion of triboelectric probes in general may be found in an article entitled "Contact Electrification Applied to Particulate Matter-Monitoring Devices" by Walter John, California Department of Health, Berkeley, Calif., published on page 650, in Fine Particles, Academic Press, ed. by Benjamin Liu, 1976, the disclosure of which is herein incorporated by reference. The triboelectric probes and electronics described herein operate on the principles discussed in the article referenced above.

The signal from a triboelectric probe is roughly proportional to particle mass. The probe may be positioned downstream of a high-voltage field, such as a field that charges the particle surface areas by corona effect. On this basis, the probe signal may be simulated using a spreadsheet or look-up table to model the probe signal behavior on the basis of empirical data.

DETAILED DESCRIPTION

Figure 1:
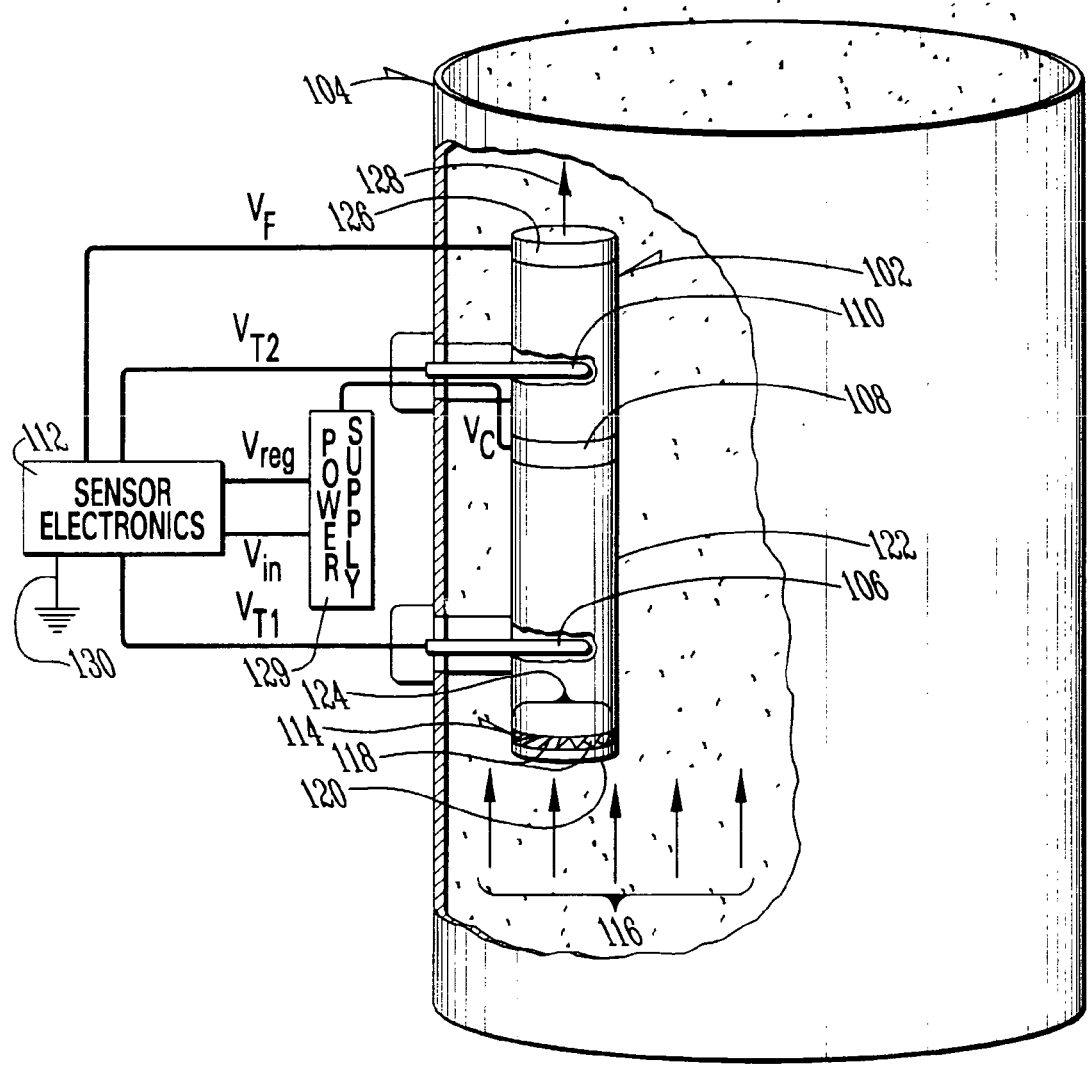
FIG. 1 illustrates a particle monitoring device or apparatus.

FIG. 1 illustrates one concept for a monitoring system according to the instrumentalities described herein. The description is by way of example, not by limitation.

As shown in FIG. 1, a tubular monitoring device 102 is mounted inside a flue or stack 104 that contains, in series, a first triboelectric probe 106, a corona charger 108 capable of providing a high voltage field, and a second triboelectric probe 110. Sensor electronics 112 receive signals $V_{T1}$ and $V_{T2}$, respectively, from the first and second triboelectric probes 106, 110. The signals $V_{T1}$ and $V_{T2}$, are electrical currents that represent particle impingement upon the respective triboelectric probes, 106, 110. Sensor electronics use the signals $V_{T1}$ and $V_{T2}$ in calculations to determine particle measurement information. An optional blower 114 imparts motive force directing particle-laden air 116 into stack 104 by the action of fan blades 118. While installation of blower 114 within stack 104 remains an option, blower 114 is not usually deployed within stack 104. This is because the flow of gas within stack 104 is sufficiently high to force particle laden air into contact with monitoring device 102. Blower 114 is usually deployed when monitoring device resides outside of stack 104, for example, in a position where monitoring device can be used to monitor ambient air or other situations where the flow of gas may be low. Mouth 120 of tube 122 samples a portion of particle-laden air 116 across area 124. An optional flowmeter 126, such as a positive displacement meter, provides a signal $V_F$ from which sensor electronics 112 can calculate or determine the flow rate of air 128 exiting tube 122. Optional flowmeter 126 is particularly desirable when blower 114 is installed.

A power supply 129 produces a voltage $V_c$ that drives corona charger 108. Voltages may vary, for example, between 500 and 50,000 volts. It is preferred to create a field strength between at least 1,000 and 20,000 volts per inch within the section of tube 122 surrounded by corona charger 108. the effect of this field is to charge particles within particle-laden air 116 so that the signal $V_{T2}$ is a function of particle surface area, such as a function where signal $V_{T2}$ is proportional to particle surface area. Sensor electronics 112 may include a conventional feedback loop that operates on a sensed signal $V_{in}$, which is also $V_c$, and uses a signal $V_{reg}$ to control $V_c$ within acceptable parameters.

Alternate mounting locations for monitoring device 102 include the tube 122 mounted outside the stack 104 and designed for stack gas to be aspirated from the stack, through the tube, and back into the stack. Monitoring device 102 utilizes blower 114 and, consequently, is an "active" collection device, while one not employing a blower 114 is a "passive" collection device. Passive sample collection does not employ any additional physical or chemical means during the collection process other than the direct contact of the monitoring device with the air to be monitored.

The particle-laden air 116 to be monitored may be directed into tube 122 and/or stack 104 by any number of means. It is not necessary to use stack 104, and tube 122 may be deployed in isolation as an ambient air sensor. As shown in FIG. 1, the particle-laden air 116 is directed through tube 122. The contacting process of the air with the device during the collection process may be either active when blower 114 is active or passive when blower 114 is not active. Blower 114 may be optionally relocated, reduced size, to the mouth 120 of tube 122 or other locations on tube 122.

Continuous monitoring for the presence of particulate matter using monitoring device 102 allows for monitoring under existing or normal physical conditions in the environment of use. The term "normal" refers to the existing physical conditions, such as temperature and pressure. Particulate matter includes matter that is not normally gaseous, as well as matter that has achieved an airborne state. This particulate matter may further be delineated as biological or non-biological. Examples of biological matter include both microscopic organisms, such as bacteria, viruses, and fungi, and non-microscopic organisms, such as airborne insects.

The size of the sampling device or tube is not critical, but is generally tailored to fit the overall size of the triboelectric probes and the duct or stack it may be mounted within. Preferred for use in many embodiments is a six inch diameter tube between about one to about three feet in length.

Monitoring device 102 may be mounted to any surface or structure by any permanent or non-permanent structure.

During passage of the particle-laden air 116 through tube 122, sensor electronics 112 collect and analyze the electronic signals $V_{T1}$ and $V_{T2}$ or analogous digital data from the respective triboelectric probes, 106, 110.

The monitoring device 102 is calibrated before use to ensure accuracy. In calibration, a control or baseline is established by exposure of monitoring device 102 to an air sample containing known particulate concentrations of known particle size distribution for a fixed sampling time followed by analysis. This procedure may also verify the effectiveness of the monitoring device. The nonlimiting example below shows one method of calibration.

EXAMPLE 1

Calibration for Leak Emission Rate Apparatus

Figure 2:
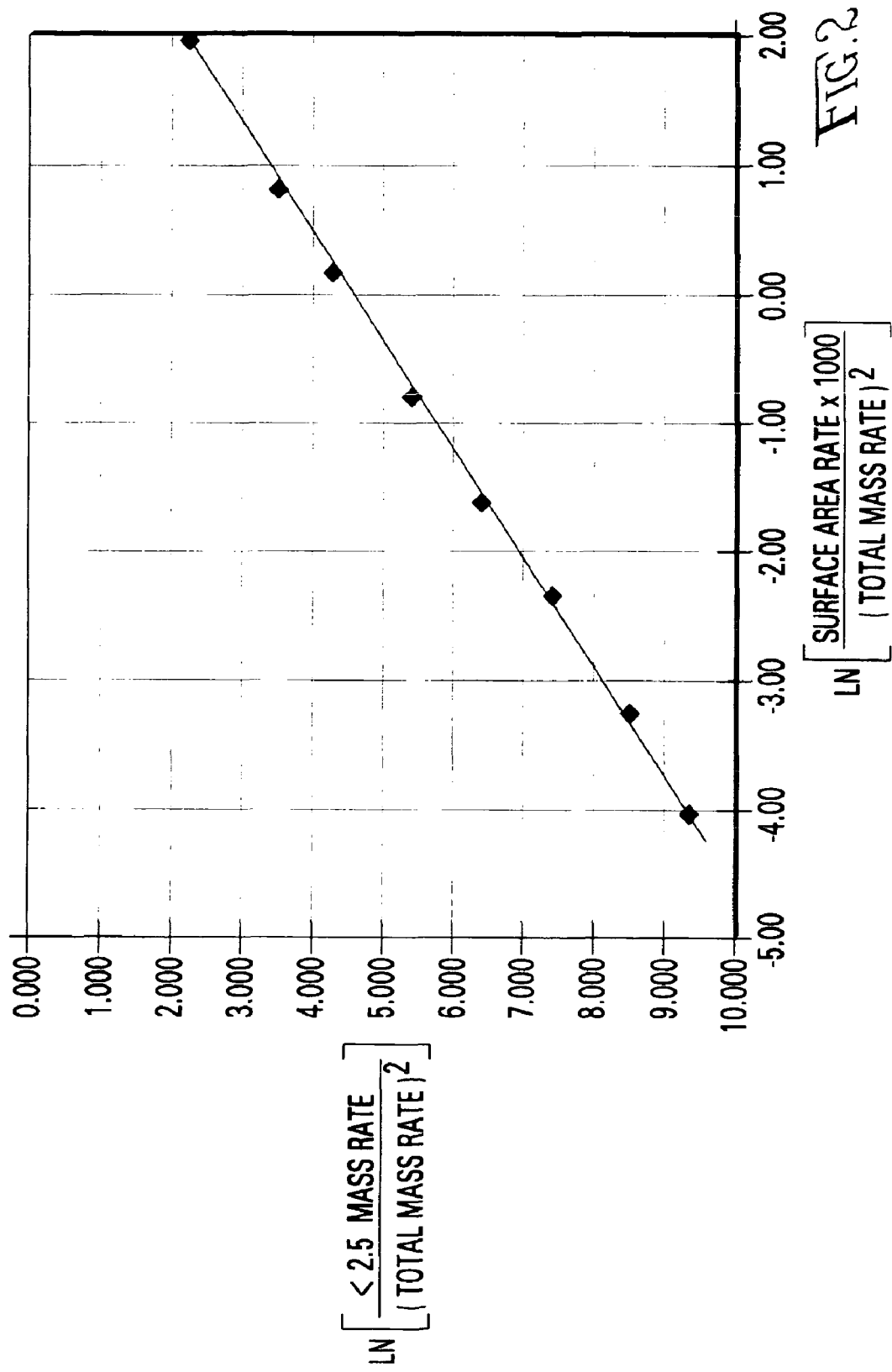
FIG. 2 illustrates a plot of surface to mass ratio versus total mass rate of particles.

Particle size distribution data were collected from twelve inlets and three outlets of a fabric filter on a rotary dryer used to process bentonite. Particles were obtained by trapping, and the size distribution data were obtained by cascade impactor measurements. These data are shown in FIG. 2. On average, the twelve inlets each had a concentration of 0.259 grams of bentonite particles per cubic meter of air at standard conditions of 60° F. and 14.73 psia. The three outlets had an average concentration of 0.047 g bentonite per standard cubic meter of air. Particle size distributions for the inlets averaged about 0.7% of particles having a nominal diameter of less than 2.5 microns, whereas the outlets averaged about 10% of particles having a nominal diameter less than about 2.5 microns. The measured outlet distribution for the fabric filter represents baseline emissions for a well-operated fabric filter. The measured inlet distribution represents the emissions that would escape through a bag leak, for example, if the bag were torn.

Intermediate points on the continuum between the outlet of the well operated fabric filter and the complete leak of the inlets were defined as partial leaks. A spreadsheet was created to create a mathematical model relating partial leaks to signal measurements along this continuum using the measured particle size distributions and total particle mass measurements, the spreadsheet calculated the mass of $PM_{2.5}$ particles and the ratio of particle surface area to total mass. Signals from the instrumentation were calculated by inverting the calibration functions of the instruments. Specifically, this inversion generated a calculated signal value for each of triboelectric probes 106, 110 based upon the calculated particle content at various points on the continuum between the inlets and the outlets. Surface area calculations assumed spherical particles centered at a nominal diameter for a distribution range at each point in the continuum. The spreadsheet allowed the baseline emission rate, the leak mass emission rate, and the particle density to be varied.

Figure 3:
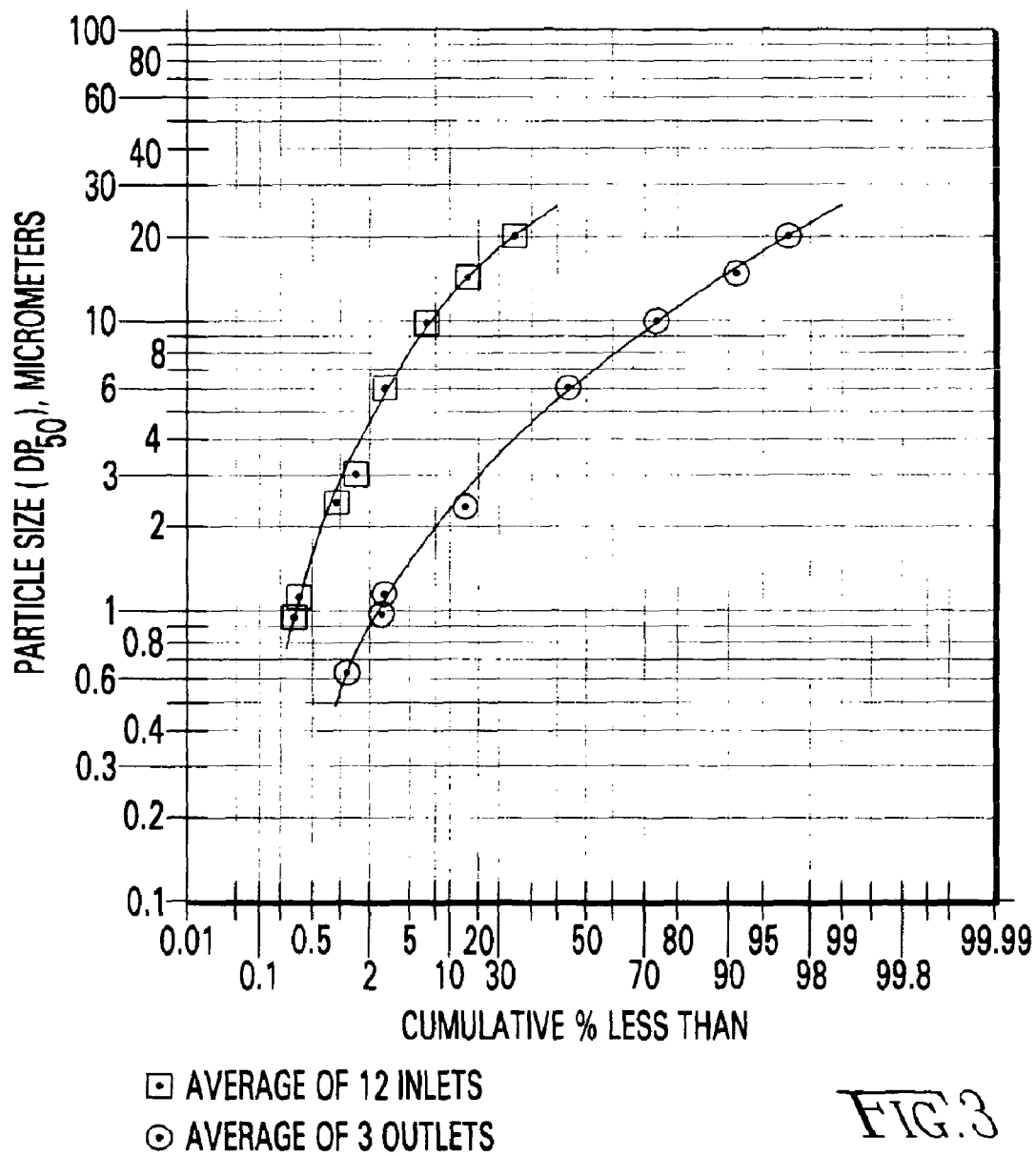
FIG. 3 illustrates particle size distribution data based on bentonite particle emission monitoring of a rotary gas dryer.

The leak mass emission rate was varied to arrive at different points on the continuum. These calculations provided a series of data points with varying leak rates while holding the baseline rate and particle density constant. The leak rates were varied in increments over a range of 1 to 100 times the baseline rate of 0.047 g/m$^3$. The surface area to total mass (S/M) ratio and the total mass rate of particles <2.5 microns in diameter (PM 2.5) were calculated and plotted in various ways until a best fit was obtained. A best fit for a straight line was achieved by plotting a quantity $$\ln(AV_{T2}/V_{T1}^2) \qquad \text{Equation (1)}$$

$$\ln(X_Y/V_{T1}^2), \qquad \text{Equation (2)}$$

where A is a scale adjustment factor, such as 1000, $V_{T2}$ represents a signal that is proportional to surface area rate of particle impaction, for example, as measured by second triboelectric probe 110; $V_{T1}$ represents a signal that is proportional to total mass rate of particle impaction, for example, as measured by triboelectric probe 106; $X_Y$ represents a fraction of total particles that present a nominal diameters less than a delimiting value Y, where the data in FIG. 3 is based upon Y being 2.5 microns; and ln is a natural logarithm. $X_Y$ is usually proportional to $V_{T1}$.

More generally, the relationships shown in Equations (1) and (2) may be represented as:

$$\log(AS_A/M_T^2) \qquad \text{Equation (3)}$$

$$\log(X_Y/M_T^2), \qquad \text{Equation (4)}$$

where A is a scale adjustment factor; $S_A$ is a surface area flowrate representing the surface area of all detectable particles, $M_T$ is a total particulate mass flow rate, and log is a logarithm to any base, such as 10 or e.

The R square value for a first order least squares fit of the data shown in FIG. 3 was 0.9997. FIG. 2 illustrates the plot. This evaluation demonstrates the feasibility of relating fine particle emissions to a surface area to mass ratio.

It will be appreciated that the linear function shown in context of FIG. 3 may be best fit by a curve of different order, e.g., a second or third order least squares fit, if the particulate source has a nonuniform leakage rate. For example, in a passive urban monitor setting, one day the particulates may be predominantly dust, and pollen or smog may dominate on another day. Monitor device 102 may be calibrated in any setting using the aforementioned technique, generally, of comparing empirical signals to known particle size distributions.

EXAMPLE 2

Calibration for Passive Atmospheric Sampler

Baseline calculations may be obtained using, for example, the aerodynamic particle sizer (APS) Model 3310 sold by TSI Inc. of St. Paul, Minn., which is described by Wilson, J. C. and Liu, B. Y. H., J. Aersol. Sci. 11:139–150 (1980); and Baron, P., Aerosol Sci. and Technol. 5:56–67, (1985). These measurements may be performed in parallel or series flow configuration with monitoring device 102. The baseline functions are mapped to the signal output of triboelectric probes 106, 110, relating the signal outputs from triboelectric probes 106, 110 to actual mass and particle size distributions in ambient air. The mapping may be, for example, by a least squares fit of any order using Equations (3) and (4), or an adaptive artificial intelligence algorithm including a neural network. The mapping function may take into account additional factors, such as measurements from a variety of sources. For example, conventional pollen counts and dust counts obtained by any means may be included as input to the model. Once monitoring device 102 is calibrated in this manner, the mapping function receives signal outputs from triboelectric probes 106, 110, and uses these signal outputs to calculate particle mass and size distribution information that describe ambient air.

EXAMPLE 3

Calibration for Other Environments of Use

Calibration for other environments of use may be done in whatever specific application is selected. By way of example, example, monitoring device may be provided for use as an ambient air monitor in a flue stack, a clean room, or a biological or chemical laboratory. The monitoring device is installed with various options described above, as may be useful in the environment of use. Calibration commences by measuring particle sizes through other suitable instrumentation, for example, instruments that may be more difficult to maintain or expensive to produce or using a combination of instruments capable of measuring a wide range of particle sizes. For example, a cascade impactor or another instrument may provide a basis for calibration.

Calibration techniques may vary with the environment of use. For example, different environments may contain particles having different shapes, sensitivities, and origins, such as biological, organic and inorganic origins. The calibration basis derived form other instrumentation may be used for calibration purposes, as in the foregoing examples. Alternatively, the calibration basis may be combined with simultaneous actual measurements from monitoring device 102 and an artificial intelligence algorithm may be used for calibration.

Those skilled in the art appreciate that the foregoing discussion illustrates a preferred embodiment. The monitoring device may be altered in insubstantial ways, yet still be constructed according to the scope and spirit of the invention. Accordingly, the inventor hereby states his intention to rely upon the Doctrine of Equivalents.

I claim:

1. A method for monitoring the mass flow of particles of a specified size fraction in a gas stream which comprises:
    (a) contacting or passing near the first triboelectric probe with a flowing particle-laden gas to obtain a first signal that embodies particle mass flow rate information;
    (b) charging particles in the particle-laden gas to produce a surface charge on the particles;
    (c) impinging the charged particles upon or passing near a second triboelectric to produce a second signal representative of particle surface area; and
    (d) analyzing the relationship between the first signal and the second signal to ascertain information concerning sizes of particles in the particle-laden gas.

2. The method of claim 1, wherein the steps (a) through (c) are performed continuously over an interval of time.

3. The method of claim 1, wherein the steps (a) through (c) are performed serially.

4. The method of claim 1, wherein the particle-laden gas comprises air.

5. The method of claim 4 wherein the information concerning sizes of particles in the particle-laden gas includes a percentage of particles having nominal diameters less than a delimiting value.

6. The method of claim 5, wherein the delimiting value is 2.5 microns.

7. The method of claim 1, wherein the steps (a) through (c) are performed as passive monitoring steps that do not require motive means to actuate the particle-laden gas.

8. The method of claim 1, further comprising a step of using motive means to actuate the particle-laden gas.

9. The method of claim 1, wherein the particles comprise biological materials.

10. The method of claim 1, wherein the particles comprise chemical materials.

11. The method of claim 1, wherein the particles comprise inorganic materials.

12. A device for monitoring air quality, comprising:
    a first triboelectric probe configured to produce a first signal when gas-borne particulates contact or pass close to the probe;
    means for charging particles in a particle-laden gas, the means for charging being positioned to avoid impingement of charged particles on the first triboelectric probe, but also to charge essentially the same gas-borne particulates contacting the first triboelectric probe; and
    a second triboelectric probe positioned such that charged particles produced by the means for charging contact or pass close to it and produce a second signal.

13. The device of claim 12, wherein the first triboelectric probe, the means for charging, and the second triboelectric probe are positioned sequentially in that order.

14. The device of claim 12, wherein the particle-laden gas affected by the charging means comprises air.

15. The device of claim 12, further comprising sensor electronics configured to operate on the first signal and second signal to ascertain information about the gas-borne particulates.

16. The device of claim 15, wherein the sensor electronics contain program instructions calibrating the device for biological materials.

17. The device of claim 15, wherein the sensor electronics contain program instructions calibrating the device for organic materials.

18. The device of claim 15, wherein the sensor electronics contain program instructions calibrating the device for inorganic materials.

19. The device of claim 15 wherein the information includes a percentage of particles having nominal diameters less than a delimiting value.

20. The device of claim 19, wherein the delimiting value is 2.5 microns.

21. The device of claim 15, wherein the sensor electronics are configured to determine a ratio of the first signal and the second signal to facilitate ascertaining the information.

22. The device of claim 12, without motive means to actuate the particle-laden gas.

23. The device of claim 12, further comprising motive means to actuate the particle-laden gas.

* * * * *